(12) United States Patent
Moretti

(10) Patent No.: US 6,487,891 B2
(45) Date of Patent: *Dec. 3, 2002

(54) APPARATUS FOR MEASURING THE MOISTURE VAPOR TRANSMISSION RATE OF A SHOE

(75) Inventor: Mario Polegato Moretti, Crocetta Del Montello (IT)

(73) Assignee: Nottington Holding B.V., Amsterdam (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/482,639

(22) Filed: Jan. 13, 2000

(65) Prior Publication Data
US 2002/0043098 A1 Apr. 18, 2002

(30) Foreign Application Priority Data
Jan. 14, 1999 (IT) .......................... 99A000011

(51) Int. Cl.⁷ .............................. G01N 15/08
(52) U.S. Cl. .................................. 73/38; 73/7
(58) Field of Search ................. 73/38, 73, 76, 73/849; 12/41.1

(56) References Cited

U.S. PATENT DOCUMENTS

| | | | | |
|---|---|---|---|---|
| 1,015,291 A | * | 1/1912 | Byrnes | |
| 1,848,697 A | * | 3/1932 | Costigan | |
| 2,048,837 A | * | 7/1936 | Byers | 12/17 |
| 2,294,512 A | * | 9/1942 | Neiman | 73/51 |
| 3,348,395 A | * | 10/1967 | Orr, Jr. et al. | 73/38 |
| 3,810,270 A | * | 5/1974 | Newman | 12/41.1 |
| 4,432,223 A | * | 2/1984 | Paquette et al. | 73/7 |
| 4,509,361 A | * | 4/1985 | Johnson | 73/73 |
| 4,838,705 A | * | 6/1989 | Byers, Jr. et al. | 374/14 |
| 4,918,981 A | * | 4/1990 | Gore | 73/76 |
| 4,961,339 A | * | 10/1990 | Kleis et al. | 73/73 |
| 5,219,121 A | * | 6/1993 | Fox et al. | 239/43 |
| 5,633,435 A | * | 5/1997 | Johnson | 73/38 |
| 5,979,235 A | * | 11/1999 | Kurz et al. | 73/432.1 |

FOREIGN PATENT DOCUMENTS

EP     0 837 329 A1  *  4/1998  ..........  G01N/33/36

* cited by examiner

*Primary Examiner*—Hezron Williams
*Assistant Examiner*—Charles D. Garber
(74) *Attorney, Agent, or Firm*—Oblon, Spivak, McClelland, Maier & Neustadt, P.C.

(57) ABSTRACT

An apparatus for measuring the moisture vapor transmission rate of a shoe comprising, on a supporting footing, a hollow body made of self-supporting material, which reproduces the shape of a foot and is designed to support the shoe to be tested. The body is provided with through holes which are distributed thereon and contains water. The apparatus also comprises a sock made of waterproof and vapor-permeable material, arranged so as to enclose the hollow body. There is also a presser by means of which the hollow body is made to perform a relative movement between a configuration in which it is spaced from and a configuration in which it is compressed against the sole of the shoe. Conditioning fixtures are also provided for heating the water in the hollow body to a preset and constant temperature, and a weighing device B for measuring the weight of the body, with all the items associated therewith, and the shoe to be tested.

19 Claims, 3 Drawing Sheets

APPARATUS FOR MEASURING THE MOISTURE VAPOR TRANSMISSION RATE OF A SHOE

BACKGROUND OF THE INVENTION

The present invention relates to an apparatus for measuring the moisture vapor transmission rate of a shoe.

The systems currently used to measure the moisture vapor transmission rate of items of clothing or shoes relate exclusively to the materials that compose them.

They allow to obtain data related to the moisture vapor transmission rate, defined in milligrams per square centimeter per hour or in grams per square centimeter per day.

The basic conditions of the tests are defined, for example, in the UNI 8429 standard, but they cannot be applied for example to an entire shoe, since they do not include the necessary conditions, such as the presence of multiple layers, foot movement and the different perspiration production conditions.

A complex simulation system has also been devised which is based on measuring the difference in moisture vapor transmission rate between a water-resistant but not vapor-permeable item and an item provided with a waterproof and vapor-permeable membrane.

This system is described for example in U.S. Pat. No. 4,918,981, which indeed relates to a method and an apparatus for testing items of apparel to be worn, such as for example shoes, gloves, et cetera which define closed elements, for the transmission of the vapor produced by perspiration.

The apparatus comprises a thin, flexible and waterproof closed liner which is highly vapor-permeable, is inserted in the item to be tested and is filled with water.

The water can be heated in order to simulate the temperature of the body and produce a high concentration of moist vapor inside the item.

The amount of moisture transferred to the environment outside the tested item as well as the amount of moisture absorbed and condensed in said item can be measured by virtue of weight differences on measurements performed before, during and after the test period.

The application of this system to shoes, however, does not yield uniform and convincing results, because the actual operating conditions to which the foot is subjected, particularly during walking and/or running, are not simulated, and because the microclimate that is produced inside a shoe dunng use is not reproduced.

SUMMARY OF THE INVENTION

The aim of the present invention is to provide an apparatus for measuring the moisture vapor transmission rate of a shoe which is capable of evaluating the amount of vapor evaporated toward the outside, the amount of vapor absorbed by the components of the shoe and the amount of moisture in contact with the foot absorbed by the inner sole, all this in dynamic conditions which simulate the movement of the foot.

Within the scope of this aim, a consequent primary object is to provide an apparatus which can measure the moisture vapor transmission rate of the sole, of the type described in EP- 382904, fitted on a shoe.

A further object is to provide in apparatus which is capable of simulating as accurately as possible the human foot and the microclimate that is produced inside a shoe.

Another object is to provide an apparatus which is structurally simple and easy to use.

This aim, these objects and others which will become apparent hereinafter are achieved by an apparatus for measuring the moisture vapor transmission rate of a shoe according to the present invention, characterized in that it comprises, on a supporting footing:

a hollow body made of self-supporting material, which reproduces the shape of a foot and is designed to support the shoe to be tested, said body having through holes which are distributed thereon and containing water;

a sock made of waterproof and vapor-permeable material, arranged so as to enclose said hollow body;

a presser for performing relative movements with said hollow body between a configuration in which it is spaced from and a configuration in which it is compressed against the sole of the shoe;

means for heating the water in said hollow body to a preset and constant temperature.

Advantageously, means are provided for measuring the weight of said hollow body with all the items associated therewith and the shoe to be tested.

Conveniently, sensors are arranged in the shoe to be tested in order to evaluate the relative humidity in different points of the foot.

BRIEF DESCRIPTION OF THE DRAWINGS

Further characteristics and advantages of the invention will become apparent from the following detailed description of an embodiment thereof, illustrated only by way of non-limitative example in the accompanying drawings, wherein.

DESCRIPTION OF THE PREFERRED EMBODIMENTS

Figure 1:
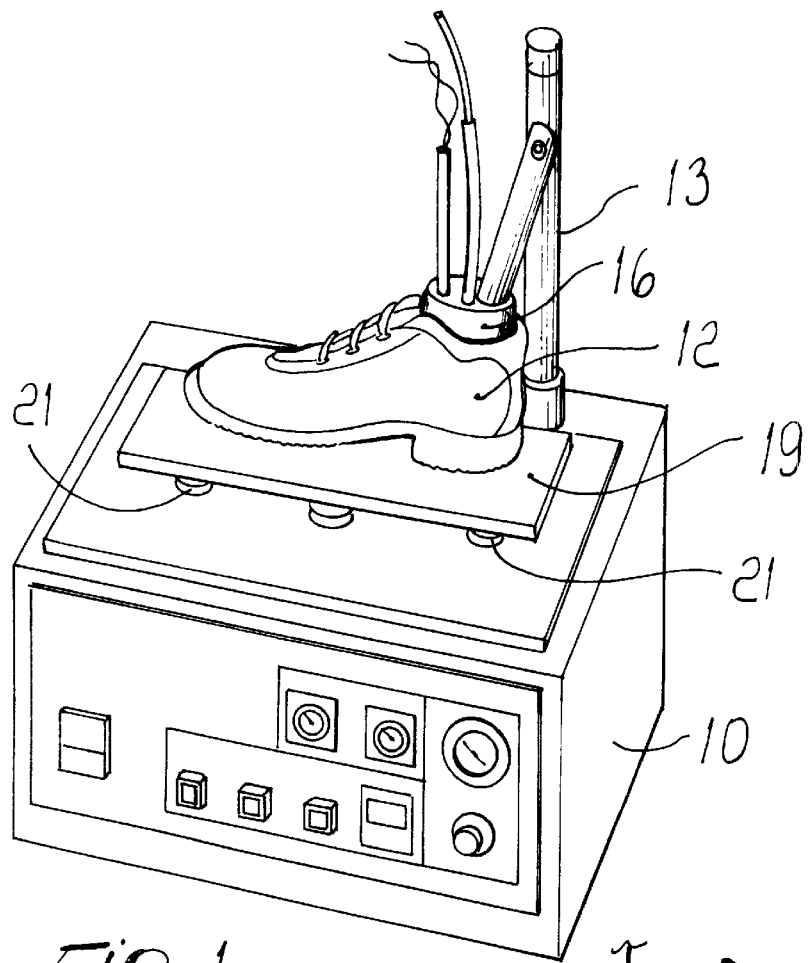
FIG. 1 is a general perspective view of the apparatus according to the invention.
Figure 2:
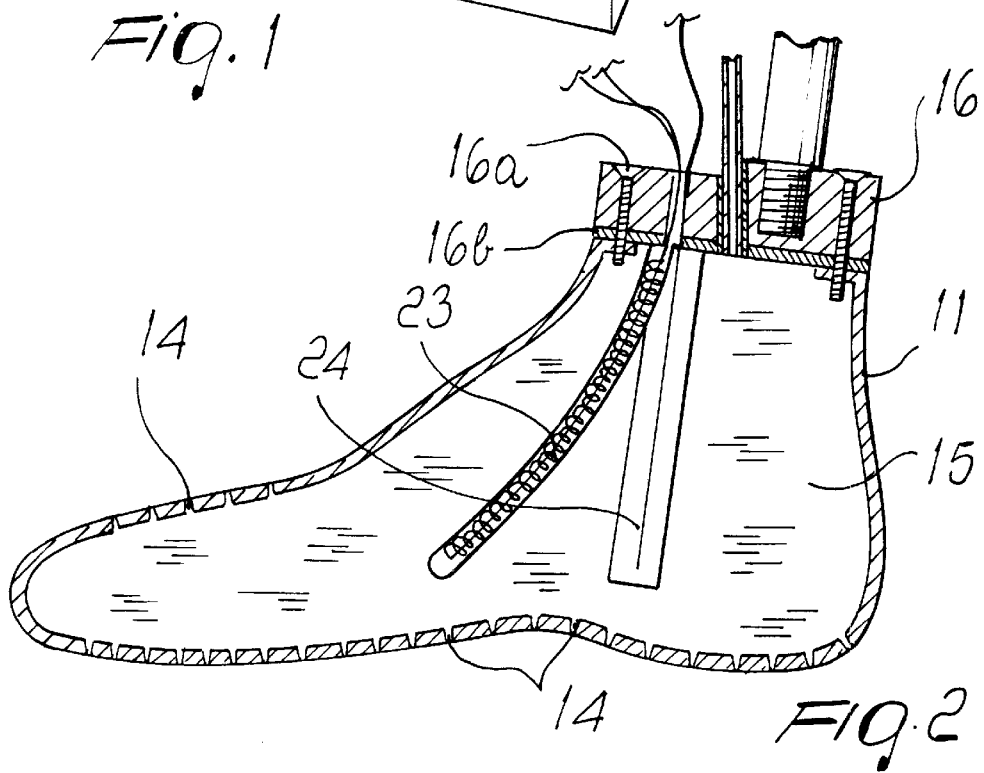
FIG. 2 is a sectional view of a hollow body which reproduces the shape of a foot and is part of the apparatus.
Figure 3:
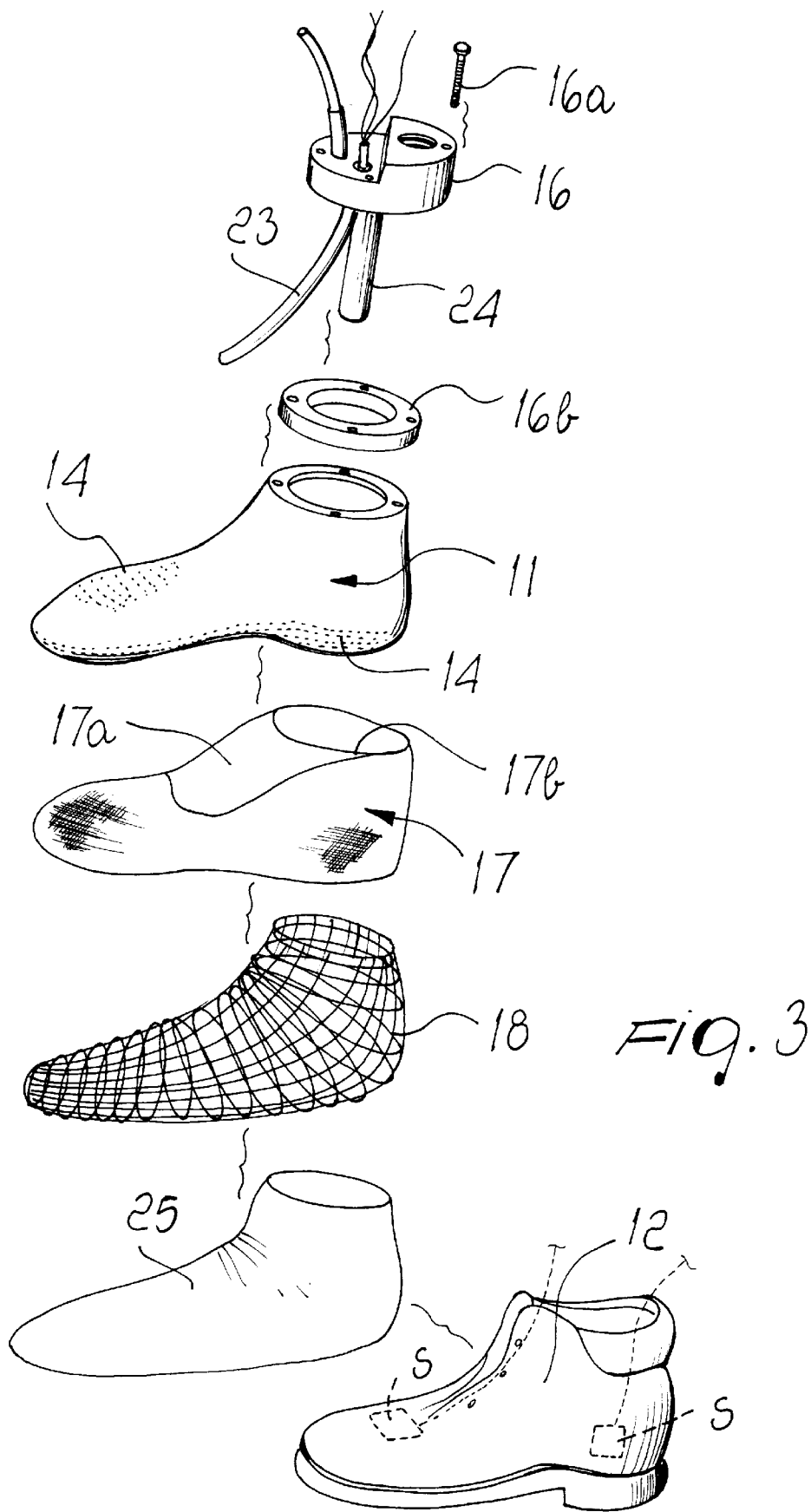
FIG. 3 is an exploded view of the hollow body of FIG. 2, including a shoe to be tested.
Figure 4:
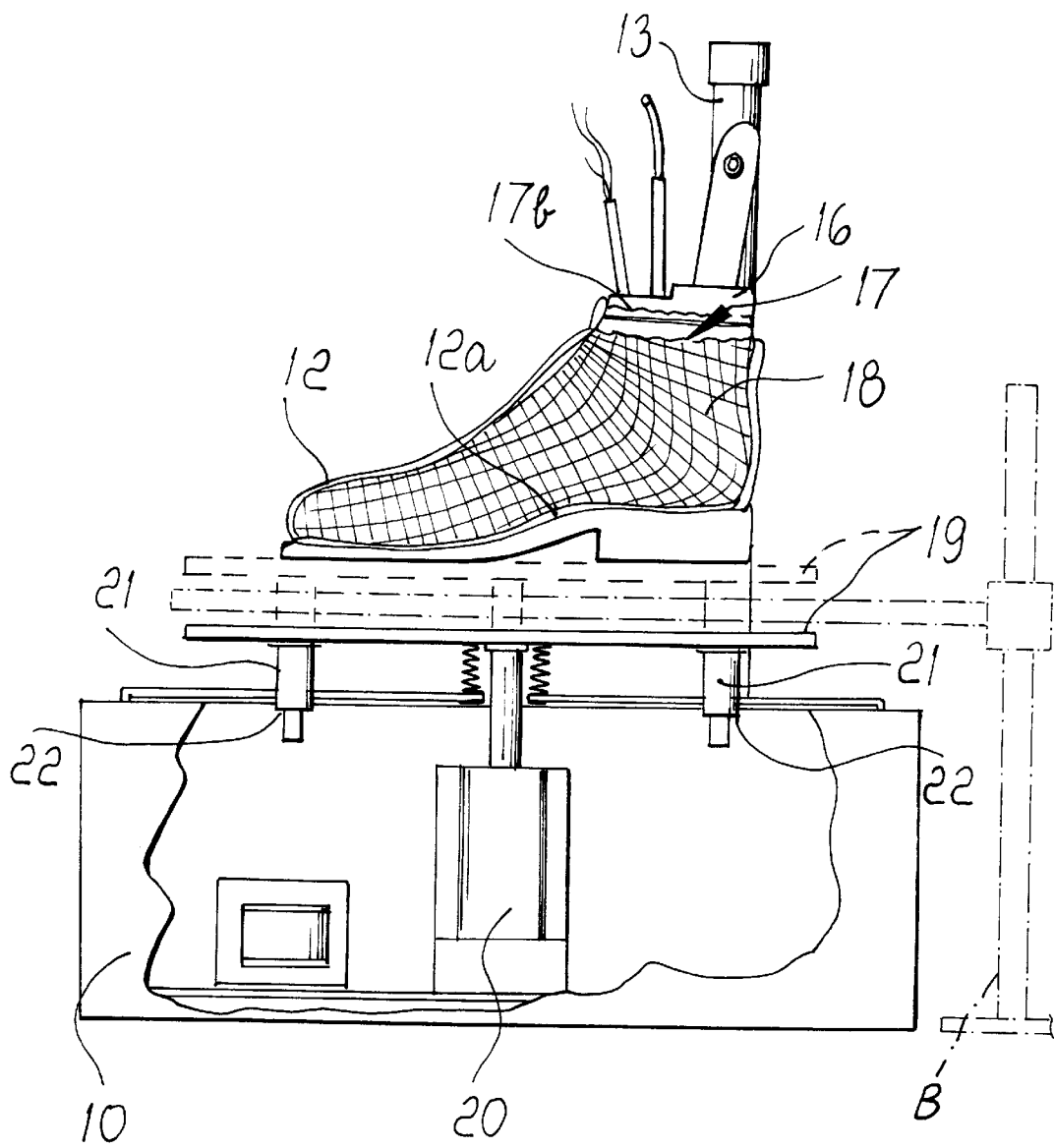
FIG. 4 is a partially cutout front view of the apparatus.

With reference to the above figures, an apparatus for measuring the moisture vapor transmission rate of a shoe comprises, on a supporting footing 10, in this case of the box-like type and containing electric measurement, control and actuation devices, a hollow body 11 made of self-supporting material, in particular steel in this case, which reproduces the shape of a foot, for supporting the shoe to be tested, designated by the reference numeral 12.

As shown in the figures, the hollow body 11 is fixed so as to be suspended from a metal post 13 which protrudes upward from the footing 10.

The hollow body 11 has through holes 14 which are distributed thereon and is filled with water designated by the reference numeral 15.

The holes 14 are distributed at least in the regions that correspond to those where the foot perspires most intensely.

The hollow body 11 is closed in an upward region, by means of screws 16a, by a cover 16 (with a sealing ring 16b) which supports the ends of the devices contained therein, which will be described hereinafter.

The apparatus further comprises a sock 17 made of waterproof and vapor-permeable material which is fitted on the hollow body 11 and is kept in contact therewith by means of a net 18.

The sock 17 is almost entirely made of non-stretch material, except for a region 17a, which corresponds to the upper part of the foot, which is made of elastic material in order to allow fitting onto the hollow body 11.

Obviously the seams must be sealed in order to prevent the passage of water.

Moreover, during fitting the upper, border 17b of the sock 17 trust be interposed between the cover 16 and the sealing ring 16b in order to also close the upward passages.

Below the hollow body 11 there is a movable surface 19 which constitutes a presser to be moved with respect to said hollow body 11 between a configuration in which it is spaced from and a configuration in which it is compressed against the sole of the shoe 12 to be tested.

In fact, the movable surface 19 is associated with an actuator 20 for causing a reciprocating translatory motion, such as a fluid-actuated cylinder, and is rigidly coupled to two rod-like elements 21, between which said actuator 20 is arranged; said rod-like elements are guided in holes 22 of the footing 10.

The apparatus also comprises conditioning means for heating the water in the hollow body 11 to a preset constant temperature; said means are constituted by an electric resistor 23 whose power supply cables exit from the cover 16.

The electric resistor 23 cooperates with a thermostat 24 which is also arranged inside the hollow body 11.

Moisture sensors S, shown schematically in the figures, are arranged inside the shoe 12 in order to evaluate the humidity in different points of the foot.

The apparatus is completed by means for measuring the weight of the hollow body 11 with all the items associated therewith and the shoe to be tested, which can be constituted by a balance B, shown schematically in dotted lines in the figures.

In practice, measurement of the moisture vapor transmission rate entails a first step, in which the hollow body 11, removed from the apparatus, is filled with water and simultaneously weighed until it reaches a weight of approximately one hundred grams.

A second step consists in fitting a sock 25, generally made of cotton, over the hollow body 11 and in weighing the assembly.

A third step consists in applying an insole 12a to the hollow body 11 and in weighing the assembly.

A further step consists in applying the shoe 12 and then weighing the assembly.

The water 15 is then heated, simulating different conditions in the body and producing the reciprocating actuation of the movable surface 19, which simulates walking.

This actuation can last three to eight hours.

Thereafter, the operations for weighing the hollow body 11 complete with all its contents, the shoe 12, the insole 12a and the sock 25 that it supports, for weighing the hollow body 11 with the insole 12a and the sock, and for weighing the hollow body 11 with the sock 25 and of the hollow body 11 alone are repeated.

All these operations must be performed in a conditioned room with constant temperature and humidity.

The results are constituted by the differences in weight between the beginning and the end of the test and they yield:

the amount of vapor that has left the hollow body 11 during the test period;
the amount of vapor absorbed by the shoe 12;
the amount of vapor absorbed by the insole 12a and by the sock 25;
the amount of evaporated and therefore transmitted vapor;
the percentage of humidity in different points in contact with the hollow body 11 during the test.

By using different shoes it is possible to evaluate the different moisture vapor transmissions and absorption capacities.

By using identical shoes modified in some points, for example by taking a shoe with a plain rubber sole and a shoe with a sole according to EP382904, it is possible to evaluate the differences and therefore the modifications occurring in one with respect to the other.

The main problem is essentially the lack of variability of the perspiration of the mechanical foot constituted by the hollow body 11 with respect to the human foot.

In particular in the presence of a vapor-permeable sole and of an internal microclimate with less than 100% humidity, the production of vapor by the foot is greatly reduced because the temperature does not rise.

If the produced vapor is not dissipated and saturation occurs (100% humidity), the condensation process generates heat and warms the foot; therefore, the lack of evaporation does not allow the foot to cool, and this worsens the situation.

The vapor transmission rate test must therefore be always combined with a thermographic and humidity test in order to provide correct data.

In practice it has been observed that the intended aim and objects of the present invention have been achieved.

An apparatus for measuring the moisture vapor transmission rate of a shoe has in fact been provided which is capable of evaluating the amount of vapor evaporated toward the outside, the amount of vapor absorbed by the components of the shoe and the humidity in contact with the foot and absorbed by the inner sole, all this occurring in dynamic conditions which simulate the movement of the foot and also simulate the microclimate that is produced inside a shoe.

This apparatus is therefore also capable of measuring the moisture vapor transmission rate of a sole, of the type described in EP-382904, fitted to a shoe.

The invention thus conceived is susceptible of numerous modifications and variations, all of which are within the scope of the inventive concept.

All the details may furthermore be replaced with other technically equivalent elements.

In practice, the materials used, so long as they are compatible with the contingent use, as well as the dimensions, may be any according to requirements.

The disclosures in Italian Patent Application No. PD99A000011 from which this application claims priority are incorporated herein by reference.

What is claimed is:

1. An apparatus for measuring the moisture vapor transmission rate of a shoe, comprising:

a hollow body made of self-supporting material, which reproduces the shape of a foot and is adapted to support the shoe to be tested, said body being adapted for containing water and having through holes which are distributed thereon for allowing water contained in the body to flow through the through holes;

a sock made of waterproof and vapor-permeable material, arranged about the hollow body so as to enclose said hollow body;

a presser configured to perform relative movements with said hollow body between a configuration in which the presser is spaced from a sole of the shoe supported by the hollow body enclosed within the sock and a configuration in which the presser is compressed against the sole of the shoe supported by the hollow body enclosed within the sock;

a conditioner configured to heat water contained in said hollow body to a preset and constant temperature; and a device configured to weigh the hollow body, with the sock associated therewith, and the shoe to be tested;

wherein the sock is almost entirely made of nonstretch material except for a region which corresponds to an upper part of the foot, which is made of elastic material in order to allow fitting over said hollow body, and wherein regions joining various parts of the sock are sealed in order to prevent the passage of water.

2. The apparatus according to claim 1, further comprising:

a plurality of humidity sensors arranged at different points in the shoe to be tested.

3. The apparatus according to claim 1, wherein the hollow body is made of steel.

4. The apparatus according to claim 1, wherein the through holes of said hollow body are distributed at least in regions that correspond to regions of the foot that perspire most intensely.

5. The apparatus according to claim 1, further comprising a net that encloses said sock.

6. The apparatus according to claim 1, wherein said conditioner is an electric resistor which heats the water in the hollow body.

7. The apparatus according to claim 6, wherein said conditioner further comprises a thermostat which keeps constant a temperature of the water heated in the hollow body.

8. The apparatus according to claim 7, wherein said hollow body is closed hermetically in an upward region by a cover from which ends of said conditioner protrude.

9. The apparatus according to claim 8, wherein an upper border of said sock is interposed, upon fitting, between said cover and a sealing ring in order to close upward water passages.

10. An apparatus for measuring the moisture vapor transmission rate of a shoe, comprising:

a hollow body made of self-supporting material, which reproduces the shape of a foot and is adapted to support the shoe to be tested, said body being adapted for containing water and having through holes which are distributed thereon for allowing water contained in the body to flow through the through holes;

a sock made of waterproof and vapor-permeable material, arranged about the hollow body so as to enclose said hollow body;

a presser configured to perform relative movements with said hollow body between a configuration in which the presser is spaced from a sole of the shoe supported by the hollow body enclosed within the sock and a configuration in which the presser is compressed against the sole of the shoe supported by the hollow body enclosed within the sock;

a conditioner configured to heat water contained in said hollow body to a preset and constant temperature; and a device configured to weigh the hollow body, with the sock associated therewith, and the shoe to be tested;

wherein the presser is constituted by a movable surface which can slide on guides and is supported by a fluid-actuated actuator configured to alternate translatory motions.

11. The apparatus according to claim 10, further comprising a plurality of humidity sensors arranged at different points in the shoe to be tested.

12. The apparatus according to claim 10, wherein the hollow body is made of steel.

13. The apparatus according to claim 10, wherein the through holes of said hollow body are distributed at least in regions that correspond to regions of the foot that perspire most intensely.

14. The apparatus according to claim 10, wherein the sock is almost entirely made of nonstretch material except for a region which corresponds to an upper part of the foot, which is made of elastic material in order to allow fitting over said hollow body, and wherein regions joining various parts of the sock are sealed in order to prevent the passage of water.

15. The apparatus according to claim 10, further comprising a net that encloses said sock.

16. The apparatus according to claim 10, wherein said conditioner is an electric resistor which heats the water in the hollow body.

17. The apparatus according to claim 16, wherein said conditioner further comprises a thermostat which keeps constant a temperature of the water heated in the hollow body.

18. The apparatus according to claim 17, wherein said hollow body is closed hermetically in an upward region by a cover from which ends of said conditioner protrude.

19. The apparatus according to claim 18, wherein an upper border of said sock is interposed, upon fitting, between said cover and a sealing ring in order to close upward water passages.

* * * * *